United States Patent
Xu et al.

(10) Patent No.: US 10,689,321 B2
(45) Date of Patent: Jun. 23, 2020

(54) METHOD FOR SYNTHESIZING PARAPHTHALOYL CHLORIDE THROUGH CONTINUOUS FLOW IN MICROCHANNEL REACTOR

(71) Applicant: Jiangsu Yangnong Chemical Group Co., Ltd, Yangzhou, Jiangsu (CN)

(72) Inventors: Lin Xu, Jiangsu (CN); Yiming Wang, Jiangsu (CN); Bo Shao, Jiangsu (CN); Kehong Ding, Jiangsu (CN); Hui Yan, Jiangsu (CN); Chenchao Bian, Jiangsu (CN); Hui Zhao, Jiangsu (CN); Yushuang Wang, Jiangsu (CN)

(73) Assignee: Jiangsu Yangnong Chemical Group Co., Ltd, Yangzhou, Jiangsu (CN)

(*) Notice: Subject to any disclaimer, the term of this patent is extended or adjusted under 35 U.S.C. 154(b) by 0 days.

(21) Appl. No.: 16/327,336

(22) PCT Filed: Jul. 7, 2017

(86) PCT No.: PCT/CN2017/092217
§ 371 (c)(1),
(2) Date: Feb. 22, 2019

(87) PCT Pub. No.: WO2018/040745
PCT Pub. Date: Mar. 8, 2018

(65) Prior Publication Data
US 2019/0185405 A1    Jun. 20, 2019

(30) Foreign Application Priority Data
Aug. 29, 2016  (CN) .......................... 2016 1 0763380

(51) Int. Cl.
*C07C 51/60*    (2006.01)
*C07C 63/30*    (2006.01)

(52) U.S. Cl.
CPC .............. *C07C 51/60* (2013.01); *C07C 63/30* (2013.01)

(58) Field of Classification Search
CPC ................................ C07C 51/60; C07C 63/30
USPC ......................................................... 562/857
See application file for complete search history.

(56) References Cited

U.S. PATENT DOCUMENTS 4,129,594 A    12/1978   Baker et al.

FOREIGN PATENT DOCUMENTS

| CN | 101687756 A | 3/2010 | |
|---|---|---|---|
| CN | 101805257 A | 8/2010 | |
| CN | 104045498 A | 9/2014 | |
| CN | 104230839 A | 12/2014 | |
| CN | 106631769 A | * 5/2017 | ............. C07C 51/60 |
| CN | 106631769 A | 5/2017 | |

(Continued)

OTHER PUBLICATIONS

English machine translation of CN106631769 (Year: 2017).*

*Primary Examiner* — Deborah D Carr
(74) *Attorney, Agent, or Firm* — Gang Yu

(57) ABSTRACT

The disclosure provides a method for synthesizing paraphthaloyl chloride through terephthalic acid chlorination in a reaction mode of a microchannel continuous flow. Compared with an existing technology, this method has characteristics of accurate control of reaction conditions, high phosgene/triphosgene utilization ratio, low catalyst dosage, high TPA conversion ratio within few tens of seconds of reaction time, high TPC yield and the like.

10 Claims, 1 Drawing Sheet

(56) References Cited

FOREIGN PATENT DOCUMENTS

JP         S56-14652 B2    4/1981
JP         S63-30341 B2    6/1988

\* cited by examiner

METHOD FOR SYNTHESIZING PARAPHTHALOYL CHLORIDE THROUGH CONTINUOUS FLOW IN MICROCHANNEL REACTOR

CROSS REFERENCE TO RELATED APPLICATIONS

This application is a national application of PCT/CN2017/092217, filed on Jul. 7, 2017. The contents of PCT/CN2017/092217 are all hereby incorporated by reference.

TECHNICAL FIELD

The disclosure relates to the technical field of the organic synthesis, and particularly relates to a method for synthesizing paraphthaloyl chloride through a continuous flow in a microchannel reactor using terephthalic acid and phosgene/triphosgene as raw materials.

BACKGROUND

Paraphthaloyl chloride (TPC) is a white solid or a colorless acicular crystal, mainly used as a polymeric monomer of poly-p-phenylene terephthamide (p-aromatic polyamide fiber, 1414 or PPTA for short) and polysulfonamide. In addition, the TPC has a certain application in aspects of a modifier for a superpolymer, intermediates of pesticide and medical industries and the like, and prospect of development and application is extensive.

Development of the TPC in China mainly depends on development of aramid 1414, because a purity requirement to a TPC product is very high in production of the aramid, it is to be satisfied that purity is greater than 99.9%, and mono acyl chloride (TMC) is smaller than 600 ppm, Otherwise, a molecular weight, a color, a mechanical property and the like of a high-performance fiber product may be seriously affected.

There are many industrialized preparation technologies for the TPC, one of existing main technology routes is to use paraxylene as a raw material, and the other is to use terephthalic acid (TPA) as the raw material. Herein the paraxylene is used as the raw material, the paraxylene firstly reacts with a chlorine gas to prepare p-hexachloro-xylene, and the p-hexachloro-xylene is hydrolyzed or reacts with the corresponding TPA, so the TPC is obtained. Using the TPA as the raw material phosgene or thionyl chloride direct chlorination method is a technology route generally adopted by existing domestic production factories for preparing the paraphthaloyl chloride.

In CN1054062A, a technology for synthesizing TPC by TPA, PCl3 and Cl2 as raw materials is disclosed, in which a reaction time is as long as 20 hours, PCl3 consumption is high, equipment corrosivity is large, product purity is low, multiple times of reduced pressure distillation is needed, and a product yield is low. In CN104402709A, the TPA and the thionyl chloride are used as the raw materials, the thionyl chloride is a reactant and is also a solvent, which is hard to be completely removed by the reduced pressure distillation, and in a rectifying process, a side reaction easily happens with the TPC. An impurity is generated, and product quality is affected. In CN101935276A, a thionyl chloride synthesis method is also used, but quaternary ammonium salt is used as a catalyst, which is difficult to be recycled, and leads a solid waste amount and product cost increased. In CN10180527A, the TPA and a solid triphosgene are used as the raw materials, dichloroethane is used as a solvent, and an intermittent kettle-type reaction is executed. However, A utilization ratio of the solid triphosgene is low, a dosage of the catalyst is large, the consumption is high, and the solvent needs to be desolventized, which increases technology steps. In CN104045498, the TPA is used as the raw material without the solvent, the TPC is intermittently synthesized by a phosgenation method. However, the reaction time is several hours, and a phosgene utilization ratio is low. In JP2002020347, titanium tetrachloride is used as the catalyst, the TPC is synthesized by the phosgenation method. However, a price of the catalyst is high, and the catalyst is easily decomposed by heat and water. In U.S. Pat. No. 2,676,187, the TPA reacts with carbon tetrachloride and a chlorine gas to synthesize the TPC in 250 DEG C, a reaction temperature is high, and equipment requirements are rigorous. In U.S. Pat. No. 3,734,959, only the carbon tetrachloride is used as an acylating agent most, the reaction temperature is high, the reaction time is long, and a yield is low. In CN1072925A, paraxylene is used as the raw material, the TPC is synthesized through chlorination and hydrolysis. However, this route is long in process, complicated in technology, and a chlorination temperature is up to 200 DEG C or more, the equipment requirements are rigorous, a product yield is low, and purity is poor.

In conclusion, the TPC is synthesized mainly using a traditional kettle-type reaction as major, thionyl chloride and phosgenation methods (or triphosgene) are used. As to the thionyl chloride method, equipment is seriously corroded by recycling the raw material of the thionyl chloride. The product purity is low, and a standard may be achieved through several times of rectification under vacuum, which lead to a higher production cost. At the same time, recycling treatment of a by-product of SO2 is troublesome, and the environment may be polluted. As to the phosgene/triphosgene method, the reaction time is long, a utilization ratio of phosgene/triphosgene is low. The catalyst is easily decomposed and coked after heated for a long time, so a color of the catalyst is deep, which makes a recycling ratio of the catalyst low and the production cost higher.

So far, research of synthesizing paraphthaloyl chloride through terephthalic acid in a microchannel reactor continuous flow mode may not be seen yet. The disclosure provides a technology route of synthesizing the paraphthaloyl chloride through the terephthalic acid in the microchannel reactor continuous flow mode, the technical advantages of the route are that a reaction temperature, a feeding molar ratio and standing time can be accurately controlled, a dosage of the catalyst is low, reaction is completed within few tens of seconds to a few minutes, a utilization ratio of phosgene/triphosgene is high, production purity is high and the like.

SUMMARY

The disclosure aims to provide a technology for synthesizing paraphthaloyl chloride through terephthalic acid chlorination in a reaction mode of a microchannel continuous flow. Compared with an existing technology, the technology in present disclosure has the characteristics of accurate control of reaction conditions, high phosgene/triphosgene utilization ratio, low catalyst dosage, high TPA conversion ratio within few tens of seconds of reaction time, high TPC yield and the like.

A method of the disclosure for preparing paraphthaloyl chloride through the terephthalic acid chlorination in a microchannel reactor is performed according to the following steps:

(1) Preparation of Raw Materials:

Terephthalic acid is a solid in a normal temperature, not melted by heating, sublimated in 300 DEG C. And in a closed system, the terephthalic acid is melted in 425 DEG C. In order to avoid using other solvents, a product of paraphthaloyl chloride is used as a solvent, the terephthalic acid is prepared as slurry for performing a microchannel continuous flow reaction.

a. In a 2000 ml four-opening flask, the paraphthaloyl chloride is firstly melted and then the terephthalic acid and a catalyst are put into, uniform slurry is formed by stirring and mixing, and heat-preserving is performed in an oil bath of 90 DEG C.

b. In a 2000 ml four-opening flask, a solid triphosgene is put into, stirring, melting and heat-preserving are performed in the oil bath of 85 DEG G.

(2) Reaction Process:

In a reaction process, a continuous flow microchannel reactor is used TPA slurry is fed through a heat-preserving slurry pump, and phosgene is fed through a mass flowmeter (the triphosgene liquid is fed by a heat-preserving plunger pump). Two flows of the materials enter the reactor in proportion, and a mixing reaction is performed in conditions that a temperature is 100-140 DEG C, a standing time is 10-300 s, and a molar ratio of phosgene/triphosgene and the TPA is 0-40% excessively, then a TPC crude product is obtained. A tail gas is absorbed by connecting water and alkali.

A reaction principle is as follows:

A catalyst DMF and a chlorinating agent of phosgene form a Vilsmeyer reagent (a V reagent for short)

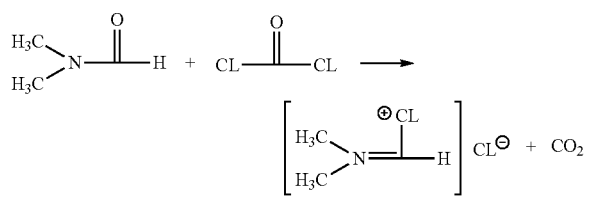

The V reagent and a carboxyl in the TPA perform a chlorination reaction so that the TPA is converted into the TPC.

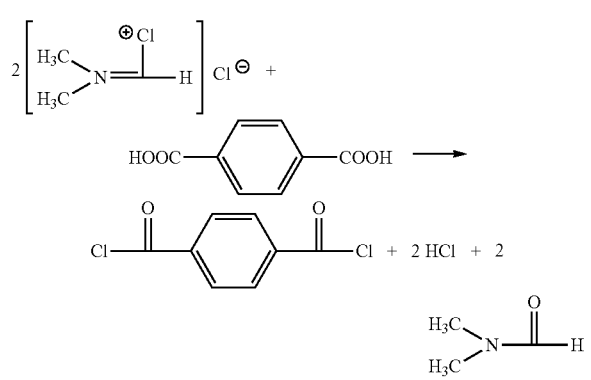

Herein, the catalyst is N,N-dimethylformamide, pyridine, and N,N-dimethylacetamide, preferably the N,N-dimethylformamide. A dosage of the catalyst is 0.1%-3% of a mass of the TPA, preferably 0.5%-3%.

In slurry preparation, a mass ratio of the TPA and the TPC is 1:1-1:10, preferably 1:1-1:5.

A molar ratio of the phosgene (or triphosgene) and the TPA is 2.0-2.8:1.

A reaction temperature is 100-140 DEG C, preferably 100-120 DEG C.

A reaction standing time is 10-300 s, preferably 30-120 s.

According to another aspect of the disclosure, a method for preparing paraphthaloyl chloride through the terephthalic acid chlorination in a microchannel reactor is performed according to the following steps:

(1) Preparation of Raw Materials:

a. firstly, a paraphthaloyl chloride is melted, and then a terephthalic acid and a catalyst are put into the paraphthaloyl chloride, a TPA slurry is obtained by stirring and mixing; and b. a solid triphosgene is melted, triphosgene liquid is obtained; or, phosgene is prepared;

(2) Reaction Process:

in the reaction process, a continuous flow microchannel reactor is used, the TPA slurry is used as a first flow of a material, the triphosgene liquid or the phosgene is used as a second flow of a material;

the first flow of the material and the second flow of the material are respectively fed into the microchannel reactor for performing a mixing reaction, then a TPC crude product is obtained, a tail gas is absorbed by connecting water and alkali.

Further, the catalyst is one or more in a group formed by N,N-dimethylformamide, pyridine, and N,N-dimethylacetamide, and a dosage of the catalyst is 0.1%-3% of a mass of the TPA.

Further, the catalyst is the N,N-dimethylformamide, and the dosage of the catalyst is 0.5%-3% of the mass of the TPA.

Further, in a preparation process of the raw materials, a mass ratio of the TPA and the TPC is 1:1-1:10.

Further, in slurry preparation, a mass ratio of the terephthalic acid and the paraphthaloyl chloride is 1:1-1:5.

Further, while the phosgene is used as the raw material, a molar ratio of the phosgene and the TPA is 2.0-2.8:1; and while the solid triphosgene is used as the raw material, a molar ratio of the solid triphosgene and the TPA is 2.0-2.8:1.

Further, in a reaction process, a reaction temperature is 100-140 DEG C.

Further, in the reaction process, the reaction temperature is 100-120 DEG C.

Further, in the reaction process, a reaction standing time is 10-300 s.

Further, in the reaction process, the reaction standing time is 30-120 s

Further, in the reaction process, the TPA slurry is fed through the heat-preserving slurry pump, the phosgene is fed through the mass flowmeter, and the triphosgene liquid is fed by the heat-preserving plunger pump.

Further, in the preparation of the raw materials, the paraphthaloyl chloride is melted, and the terephthalic acid and the catalyst are put into the paraphthaloyl chloride, uniform slurry is formed by stirring and mixing, and heat-preserving is performed in the oil bath of 90 DEG C, so the TPA slurry is obtained; stirring, melting, and heat-preserving are performed on the solid triphosgene in the oil bath of 85 DEG C, so the triphosgene liquid is obtained.

Herein the microchannel reactor is a Corning microchannel heart-shaped and straight structure, in allusion to problems existing in an existing kettle-type reaction that the utilization ratio of phosgene/triphosgene is low, the catalyst consumption is high, and the solvent is needed and the like. The disclosure provides a method for preparing TPC through performing TPA chlorination in a continuous flow reaction mode in a continuous flow microchannel reactor. The disclosure uses the TPA as the raw material, and two flows of the materials are respectively prepared, and fed into the reactor through a slurry metering pump and a phosgene flowmeter. A temperature is accurately controlled by a heat exchanger, and a reaction temperature is measured by third, fourth and ninth plate thermocouples of the reactor. In the reaction process, a feeding molar ratio is regulated through the metering pump and the phosgene flowmeter. The raw material enters the reactor through a pressure gauge, a safety valve and a one-way valve, a pressure of a reaction system is measured by the pressure gauge, the safety valve protects the reactor to execute a reaction under a certain safe pressure. The slurry enters a reaction module 3# after passing through a pre-heating plate, the phosgene (or triphosgene) directly enters the reaction module 3# for performing the reaction without pre-heating. An outlet of the reactor is connected with a counterbalance valve, so the reactor keeps a certain pressure. After few tens of seconds to a few minutes, a chlorination product are obtained at a discharging port, which comprises the TPC in upper layer and a catalyst in lower layer. Two parties are layered while hot, the catalyst is layered in time and discharged from the system, stored in a normal temperature, quantitatively analyzed and used for circularly applying, and rectification under vacuum is performed on the chlorination product to obtain a product.

Compared with an existing kettle-type technology, the disclosure has the following main features:

(1) The disclosure adopts a continuous flow microchannel reactor, a reaction time is shortened from several hours of traditional reaction time to a few minutes even few tens of seconds, and a reaction efficiency is greatly improved.

(2) The dosage of the catalyst is low, the reaction time is short, the catalyst is stable and can be circularly applied, and a recycling rate is high.

(3) The method in this disclosure is a pressurizing reaction, solubility of the phosgene/triphosgene in the reaction system is increased, and a utilization ratio of the phosgene/triphosgene is greatly improved.

BRIEF DESCRIPTION OF THE DRAWINGS

Drawings of description forming one part of the application are used for providing further understanding to the disclosure, schematic embodiments of the disclosure and description thereof are used for explaining the disclosure, and are not intended to improperly limit the disclosure. In the drawings.

DETAILED DESCRIPTION OF THE EMBODIMENTS

Figure 1:
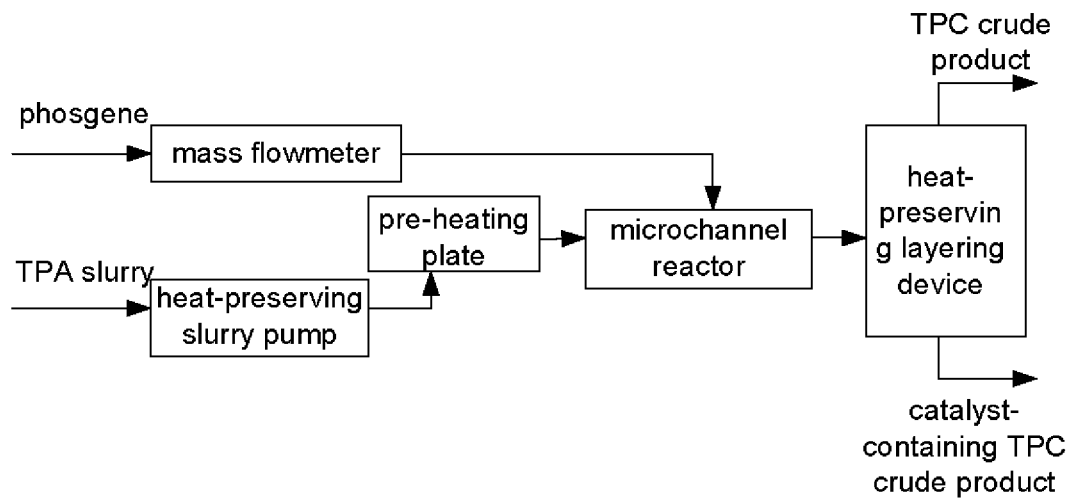
FIG. 1 shows a phosgene method technology block diagram of the disclosure.
Figure 2:
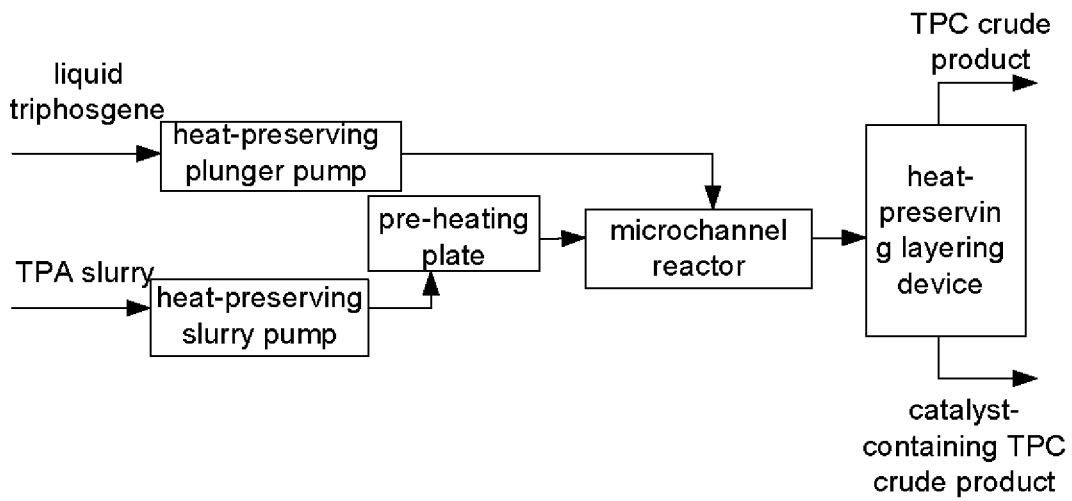
FIG. 2 shows a triphosgene method technology block diagram of the disclosure.

It is to be noted that the embodiments in the application and features in the embodiments can be mutually combined in the case without conflicting. The disclosure is described in detail below with reference to the drawings and in combination with the embodiments.

The application is further described in detail below in combination with the specific embodiments, these embodiments may not be understood to limit a scope of protection required by the disclosure.

Embodiment 1

1. Preparation of raw materials: 2000 g of TPC is weighed, and put into a 2000 ml four-opening flask. The four-opening flask is placed in an oil bath of 90 DEG C for heating and melting, and 500 g of TPA (sieving in 200 meshes in advance) and 10 g of DMF are added, uniform slurry is formed by stirring and mixing for future use. A phosgene is fed into a microreactor for future use by a pipeline through a mass flowmeter, a one-way valve, a safety valve and the like.

2. In a heart-shaped microchannel, of which a material is special glass, a method is performed according to the following steps: (1) TPA slurry enters a microchannel reactor through a heat-preserving slurry pump, a phosgene valve is opened, and the slurry enters the microchannel reactor through a mass flowmeter; (2) in a reaction process, a continuous flow microchannel reactor is used, uniform slurry of a raw material TPA is mixed with the phosgene in the reactor in proportion, a reaction is controlled to be performed in 100 DEG C through a heat exchanger; (3) a molar ratio of the TPA slurry and the phosgene is controlled to be 1:2.2, and a standing time is controlled to be 60 seconds through regulating a frequency of a slurry pump and an opening degree of a flowmeter. Two flows of the materials are mixed to react in a reaction module; (4) through regulating a counterbalance valve at an outlet of the reactor, a pressure of a reaction system is kept in 3 bar, and monitored and measured by a pressure gauge on a gas feeding pipeline; and (5) after the material passes through the microchannel reactor, a chlorination product is continuously discharged and enters a heat-preserving layering device in 85 DEG C, the upper layer is TPC liquid, a catalyst V reagent is in the lower layer, a tail gas is absorbed by connecting water and alkali. 612.0 g of an upper received material is firstly separated, 602.8 g of a fraction is collected in 128-130 DEG C through rectification under vacuum (12-13 mmHg), after 19.8 g of the yellow oily liquid V reagent separated from the lower layer is mixed with 1994.9 g of TPC liquid separated from the upper layer, a mixture is directly used for dosing and applying. A rectifying product is analyzed by UPLC: TPA is not detected, TMC is 226 ppm, gas chromatography TPC is greater than 99.9%, a melting range is 82.0-82.3 DEG C, a total yield of the product is 98.58% (calculated by the TPA), a utilization rate of the phosgene is 91%, and a recycling rate of the catalyst is 98.2% (quantitative analysis).

Embodiment 2

1. Preparation of raw materials: 2000 g of TPC is weighed, and put into a 2000 ml four-opening flask. The four-opening flask is placed in an oil bath of 90 DEG C for heating and melting, and 500 g of TPA (sieving in 200 meshes in advance) and 5 g of DMF are added, uniform slurry is formed by stirring and mixing for future use. A phosgene is fed into a microreactor for future use by a pipeline through a mass flowmeter, a one-way valve, a safety valve and the like.

2. In a heart-shaped microchannel of which a material is special glass, a method is performed according to the following steps: (1) TPA slurry enters a microchannel reactor through a heat-preserving slurry pump, a phosgene valve is opened, and the slurry enters the microchannel reactor through a mass flowmeter; (2) in a reaction process, a continuous flow microchannel reactor is used, uniform slurry of a raw material TPA is mixed with the phosgene in the reactor in proportion, a reaction is controlled to be performed in 120 DEG C through a heat exchanger; (3) a molar ratio of the TPA slurry and the phosgene is controlled to be 1:2.1, and standing time is controlled to be 30 seconds through regulating a frequency of a slurry pump and an opening degree of a flowmeter, two flows of the materials are mixed to react in a reaction module; (4) through regulating a counterbalance valve at an outlet of the reactor, a pressure of a reaction system is kept in 5 bar, and monitored and measured by a pressure gauge on a gas feeding pipeline; and (5) after the material passes through the microchannel reactor, a chlorination product is continuously discharged and enters a heat-preserving layering device in 85 DEG C, the upper layer is TPC liquid, a catalyst V reagent is in the lower layer, a tail gas is absorbed by connecting water, and absorbed by alkali. 612.0 g of an upper received material is firstly separated, 600.3 g of a fraction is collected in 128-130 DEG C through rectification under vacuum (12-13 mmHg), after 9.6 g of the yellow oily liquid V reagent separated from the lower layer is mixed with 1997.7 g of TPC liquid separated from the upper layer, a mixture is directly used for dosing and applying. A rectifying product is analyzed by UPLC: TPA is not detected, TMC is 254 ppm, gas chromatography TPC is greater than 99.9%, a melting range is 81.9-82.3 DEG C, a total yield of the product is 98.28% (calculated by the TPA), a utilization rate of the phosgene is 95.2%, and a recycling rate of the catalyst is 97.5% (quantitative analysis).

Embodiment 3

1. Preparation of raw materials: 2000 g of TPC is weighed, and put into a 2000 ml four-opening flask. The four-opening flask is placed in an oil bath of 90 DEG C for heating and melting, and 500 g of TPA (sieving in 200 meshes in advance) and 5 g of DMF are added, uniform slurry is formed by stirring and mixing for future use. A phosgene is fed into a microreactor for future use by a pipeline through a mass flowmeter, a one-way valve, a safety valve and the like.

2. In a heart-shaped microchannel of which a material is special glass, a method is performed according to the following steps: (1) TPA slurry enters a microchannel reactor through a heat-preserving slurry pump, a phosgene valve is opened, and the slurry enters the microchannel reactor through a mass flowmeter; (2) in a reaction process, a continuous flow microchannel reactor is used, uniform slurry of a raw material TPA is mixed with the phosgene in the reactor in proportion, a reaction is controlled to be performed in 120 DEG C through a heat exchanger; (3) a molar ratio of the TPA slurry and the phosgene is controlled to be 1:2.05, and standing time is controlled to be 60 seconds through regulating a frequency of a slurry pump and an opening degree of a flowmeter, two flows of the materials are mixed to react in a reaction module; (4) through regulating a counterbalance valve at an outlet of the reactor, a pressure of a reaction system is kept in 8 bar, and monitored and measured by a pressure gauge on a gas feeding pipeline; and (5) after the material passes through the microchannel reactor, a chlorination product is continuously discharged and enters a heat-preserving layering device in 85 DEG C, the upper layer is TPC liquid, a catalyst V reagent is in the lower layer, a tail gas is absorbed by connecting water, and absorbed by alkali. 612.0 g of an upper received material is firstly separated, 603.7 g of a fraction is collected in 128-130 DEG C through rectification under vacuum (12-13 mmHg), after 9.7 g of the yellow oily liquid V reagent separated from the lower layer is mixed with 1997.6 g of TPC liquid separated from the upper layer, a mixture is directly used for dosing and applying. A rectifying product is analyzed by UPLC: TPA is not detected, TMC is 315 ppm, gas chromatography TPC is greater than 99.9%, a melting range is 82.1-82.5 DEG C, a total yield of the product is 98.83% (calculated by the TPA), a utilization rate of the phosgene is 97.6%, and a recycling rate of the catalyst is 97.6% (quantitative analysis).

Embodiment 4

1. Preparation of raw materials: 2007.3 g of a TPC crude product containing a catalyst which is separated in the embodiment 3 is put into a 2000 ml four-opening flask, and placed in an oil bath of 90 DEGC for heating and melting, and 500 g of TPA (content is 99.9%, and sieved in 200 meshes in advance) is added, 0.2 g of DMF is replenished, uniform slurry is formed for future use by stirring and mixing. A phosgene is fed into a microreactor for future use by a pipeline through a mass flowmeter, a one-way valve, a safety valve and the like.

2. Reaction conditions and processes are the same as the embodiment 3, 612.0 g of an upper received material is firstly separated, 603.3 g of a fraction is collected in 128-130 DEG C through rectification under vacuum (12-13 mmHg), after 9.7 g of the yellow oily liquid V reagent separated from the lower layer is mixed with 1997.3 g of TPC liquid separated from the upper layer, a mixture is directly used for dosing and applying. A rectifying product is analyzed by UPLC: TPA is not detected, TMC is 281 ppm, gas chromatography TPC is greater than 99.9%, a melting range is 82.0-82.2 DEG C, a total yield of the product is 98.78% (calculated by the TPA), a utilization rate of the phosgene is 97.6%, and a recycling rate of the catalyst is 97.8% (quantitative analysis).

Embodiment 5

1. Preparation of raw materials: applying is the same as the embodiment 3, a phosgene reaction is replaced by liquid triphosgene, and a heat-preserving plunger pump is used for feeding.

2. Reaction conditions and processes are the same as the embodiment 3, 612.0 g of an upper received material is firstly separated, 600.7 g of a fraction is collected in 128-130 DEG C through rectification under vacuum (12-13 mmHg), after 9.9 g of the yellow oily liquid V reagent separated from the lower layer is mixed with 1997.4 g of TPC liquid separated from the upper layer, a mixture is directly used for dosing and applying. A rectifying product is analyzed by UPLC: TPA is not detected, TMC is 382 ppm, gas chromatography TPC is greater than 99.9%, a melting range is 81.9-82.5 DEG C, a total yield of the product is 98.35% (calculated by the TPA), a utilization rate of the triphosgene is 97.4%, and a recycling rate of the catalyst is 97.1% (quantitative analysis).

Embodiment 6

1. Preparation of raw materials: 2007.3 g of a TPC crude product containing a catalyst which is separated in the embodiment 5 is applied, and put into a 2000 ml four-opening flask, and placed in an oil bath of 90 DEG C for heating and melting. 500 g of TPA (content is 99.9%, and sieved in 200 meshes in advance) is added, 0.29 g of DMF is replenished, uniform slurry is formed for future use by stirring and mixing. A phosgene reaction is replaced by liquid triphosgene, and a heat-preserving plunger pump is used for feeding.

2. Reaction conditions and processes are the same as the embodiment 5, 612.0 g of an upper received material is firstly separated, 603.8 g of a fraction is collected in 128-130 DEG C through rectification under vacuum (12-13 mmHg), after 10.0 g of the yellow oily liquid V reagent separated from the lower layer is mixed with 1996.9 g of TPC liquid separated from the upper layer, a mixture is directly used for dosing and applying. A rectifying product is analyzed by UPLC: TPA is not detected, TMC is 363 ppm, gas chromatography TPC is greater than 99.9%, a melting range is 82.1-82.4 DEG C, a total yield of the product is 98.85% (calculated by the TPA), a utilization rate of the triphosgene is 96.9%, and a recycling rate of the catalyst is 97.9% (quantitative analysis).

Embodiment 7

1. Preparation of raw materials: applying is the same as the embodiment 3, a difference is as follows: after TPC is weighed, the TPC is put into a four-opening flask, and placed in an oil bath of 100 DEG C for heating and melting, and TPA and DMF are added, uniform slurry is formed for future use by stirring and mixing. A solid triphosgene is melted in 90 DEG C to form liquid triphosgene.

2. Reaction conditions and processes are the same as the embodiment 3, a difference is as follows: a reaction temperature is 145 DEG C, and reaction standing time is 10 s.

612.0 g of an upper received material is firstly separated, 596.7 g of a fraction is collected in 128-130 DEG C through rectification under vacuum (12-13 mmHg), after 12.9 g of the yellow oily liquid V reagent separated from the lower layer is mixed with 1992.4 g of TPC liquid separated from the upper layer, a mixture is directly used for dosing and applying. A rectifying product is analyzed by UPLC: TPA is not detected, TMC is 400 ppm, gas chromatography TPC is greater than 99.9%, a melting range is 82.1-82.6 DEG C, a total yield of the product is 96.83% (calculated by the TPA), a utilization rate of the triphosgene is 87.4%, and a recycling rate of the catalyst is 95.1% (quantitative analysis).

Contrast Example 1

1. Device: a kettle-type reaction.
2. Reaction: 180 g of TPC, 60 g of TPA (99.9%), and 1.8 g of DMF (99.9%) are put into a 250 ml four-opening flask, and heated to 87 DEG C, uniform slurry is formed by mixing. A phosgene is fed into a reaction flask through a mass flowmeter, a flow is about 20 g/h. The reaction is performed in 90 DEG C until the slurry becomes pale yellow clear liquid, and the reaction is stopped. Reaction time is about 6 hours, 111.2 g of phosgene is fed totally, and 255.1 g of a material is received totally. 3.2 g of a black viscous liquid V reagent is separated from the lower layer, and 73.5 g of TPC liquid is taken from the upper layer, 68.35 g of a fraction is collected in 128-130 DEG C through rectification under vacuum (12-13 mmHg), analyzed by UPLC: TPA is not detected, TMC is 812 ppm, gas chromatography TPC is greater than 99.9%, a melting range is 81.9-82.2 DEG C, a total yield of the product is 93.25% (calculated by the TPA), a utilization rate of the phosgene is 64.3%, and a recycling rate of the catalyst is 65.52% (quantitative analysis).

Contrast Example 2

1. Device: a Kettle-Type Reaction.
2. Reaction: 100 g of TPC, 25 g of TPA (99.9%), and 0.75 g of DMF (99.9%) are put into a 250 ml four-opening flask, and heated to 95 DEG C, uniform slurry is formed by mixing. A phosgene is fed into a reaction flask through a mass flowmeter, a flow is about 10 g/h. The reaction is performed in 98 DEG C until the slurry becomes pale yellow clear liquid, and the reaction is stopped. Reaction time is about 4.5 hours, 43.1 g of phosgene is fed totally, and 131.4 g of a material is received totally, 1.2 g of a black viscous liquid V reagent is separated from the lower layer, and 30.6 g of TPC liquid is taken from the upper layer, 28.5 g of a fraction is collected in 128-130 DEG C through rectification under vacuum (12-13 mmHg), analyzed by UPLC: TPA is not detected, TMC is 726 ppm, gas chromatography TPC is greater than 99.9%, a melting range is 82-82.3 DEG C, a total yield of the product is 93.15% (calculated by the TPA), a utilization rate of the phosgene is 69.2%, and a recycling rate of the catalyst is 43.48% (quantitative analysis).

Table 1 is quality indexes of industrial paraphthaloyl chloride

| Project | | | Index | |
|---|---|---|---|---|
| | | | Superior products | Top quality products |
| Paraphthaloyl chloride | w % | ≥ | 99.9 | 99.6 |
| Terephthalic acid | w % | ≤ | 0.01 | |
| Isophthaloyl dichloride | w % | ≤ | 0.01 | |
| Sum of other impurities | w % | ≤ | 0.08 | 0.30 |
| Melting point | DEG C. | | 82-83 | |

The above are merely preferable embodiments of the disclosure, and are not used for limiting the disclosure. It may be understood by those skilled in the art that the disclosure may have various changes and variations. All of any modifications, equivalent replacements, improvements and the like made within spirit and principles of the disclosure shall fall within a scope of protection of the disclosure.

What is claimed is:

1. A method for preparing paraphthaloyl chloride through terephthalic acid chlorination in a microchannel reactor, wherein the method comprises the following steps:
  (1); a preparation of raw materials:
  a. firstly melting a paraphthaloyl chloride, and then putting a terephthalic acid and a catalyst into the paraphthaloyl chloride, stirring and mixing, and conducting heat-preserving in a 90 DEG C oil bath to obtain a TPA slurry; and
  b. putting a solid triphosgene, conducting stirring, melting and heat-preserving in a 85 DEG C oil bath to obtain a triphosgene liquid;
  (2) reaction process:
  in a reaction process, using a continuous flow microchannel reactor, guiding the TPA slurry through a heat-preserving insulative slurry pump and a phosgene through a mass flow meter (the triphosgene liquid is fed using a heat-preserving plunger pump), and the two materials enter the reactor in proportion and preform a mixing reaction, to obtain a TPC crude product, absorbing a tail gas by connecting water and alkali.

2. The method for preparing the paraphthaloyl chloride through the terephthalic acid chlorination in the microchannel reactor as claimed in claim 1, wherein the catalyst is one or more in a group formed by N,N-dimethylformamide, pyridine and N,N-dimethylacetamide, and a dosage of the catalyst is 0.1%-3% of a mass of the TPA.

3. The method for preparing the paraphthaloyl chloride through the terephthalic acid chlorination in the microchannel reactor as claimed in claim 2, wherein the catalyst is the N,N-dimethylformamide, and the dosage of the catalyst is 0.5%-3% of the mass of the TPA.

4. The method for preparing the paraphthaloyl chloride through the terephthalic acid chlorination in the microchannel reactor as claimed in claim 1, wherein in a preparation process of the raw materials, a mass ratio of the TPA and the TPC is 1:1-1:10.

5. The method for preparing the paraphthaloyl chloride through the terephthalic acid chlorination in the microchannel reactor as claimed in claim 4, wherein in slurry preparation, a mass ratio of the terephthalic acid and the paraphthaloyl chloride is 1:1-1:5.

6. The method for preparing the paraphthaloyl chloride through the terephthalic acid chlorination in the microchannel reactor as claimed in claim 1, wherein while the phosgene is used as the raw material, a mole ratio of the phosgene and TPA is 2.0-2.8:1; and while the solid triphosgene is used as the raw material, a mole ratio of the solid triphosgene and the TPA is 2.0-2.8:1.

7. The method for preparing the paraphthaloyl chloride through the terephthalic acid chlorination in the microchannel reactor as claimed in claim 1, wherein in a reaction process, a reaction temperature is 100-140 DEG C.

8. The method for preparing the paraphthaloyl chloride through the terephthalic acid chlorination in the microchannel reactor as claimed in claim 7, wherein in the reaction process, the reaction temperature is 100-120 DEG C.

9. The method for preparing the paraphthaloyl chloride through the terephthalic acid chlorination in the microchannel reactor as claimed in claim 1, wherein in the reaction process, a reaction standing time is 10-300 s.

10. The method for preparing the paraphthaloyl chloride through the terephthalic acid chlorination in the microchannel reactor as claimed in claim 9, wherein in the reaction process, the reaction standing time is 30-120 s.

* * * * *